United States Patent [19]

Zikria

[11] Patent Number: 4,994,444
[45] Date of Patent: Feb. 19, 1991

[54] MACROMOLECULES FOR SEALING CAPILLARY ENDOTHELIAL JUNCTIONS

[75] Inventor: Bashir A. Zikria, Norwood, N.J.

[73] Assignee: The Trustees of Columbia in the City of New York, New York, N.Y.

[21] Appl. No.: 80,403

[22] Filed: Jul. 31, 1987

[51] Int. Cl.$^5$ ............................................. A61K 31/00
[52] U.S. Cl. ........................................ 514/60; 514/59; 514/921; 514/950
[58] Field of Search ................... 514/60, 59, 921, 950; 536/102, 112

[56]  References Cited

U.S. PATENT DOCUMENTS 3,523,938  8/1970  Hershenson et al. ............... 536/111
3,758,382  9/1973  Knorpp ................................ 514/60
4,798,824  1/1989  Belzer et al. ........................ 514/60

OTHER PUBLICATIONS

Joris, et al. (1972) *Virchows Arc*, 12:73–83 (Exhibit A).
Horan, et al. (1986) *American Journal of Pathology*, 124:570–576 (Exhibit B).
Majno, et al. (1961) *J. Biophys. Biochem. Cytol*, 11:571–605 (Exhibit C).
Lelcuk, et al. (1985) *Ann. Surg.*, 202:642–646 (Exhibit D).
Joris, et al. (1987) i Am. J. of Pathology, 126:19–24 (Exhibit E).
Grega, et al. (1986) *Fed.Proc.*, 45:75–76 (Exhibit F).
Maier, R. V., and Carrico, C. J. (1986) *Developments in Resuscitation Advances in Surgery*, 19:290 (Exhibit G).
Moggio, R. A. et al. (1983), *Crit. Care Med.*, 11:943 (Exhibit H).
Kirklin, J. K. et al. (1984) *Ann. Thorac. Surg.*, 37:40 (Exhibit I).
Diehl, H. T. et al. (1982) *Ann. Thorac. Surg.*, 34:674 (Exhibit J).
Rackow, E. C. et al. (1983) *Crit. Care Med.*, 11:839 (Exhibit K).
Puri, V. K. et al. (1982) *Crit. Care Med.*, 10:230 (Exhibit L).
Ring J., and Messmer K. (1977) *Lancet* 1:466 (Exhibit M).

*Primary Examiner*—Ronald W. Griffin
*Assistant Examiner*—Everett White
*Attorney, Agent, or Firm*—John P. White

[57]  ABSTRACT

The present invention provides compositions of matter and methods for treating a human subject to prevent leakage of serum albumin from capillary endothelial junctions during a period of increased capillary permeability. The method comprises administering to the human subject an effective capillary pore sealing amount of a macromolecule which is biodegradable, non-toxic, globular in shape, with a molecular weight range from about 100,000 daltons to about 1,000,000 daltons and a pharmaceutically acceptable carrier. The composition of matter comprises a fraction derived from hydroxyethyl starch.

12 Claims, No Drawings

MACROMOLECULES FOR SEALING CAPILLARY ENDOTHELIAL JUNCTIONS

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Current scientific literature reveals that inflammatory mediators initiate a biochemical chain of events that increase capillary permeability. Under such circumstances the separation of capillary endothelial junctions cannot keep infused colloids such as serum albumin, Dextran-40, and particular intracapillary fluids within the vessel.

Colloids such as serum albumin escape into the interstitium creating a nonfunctional "third space", the volume of which increases as albumin leakage increases. This leakage widens capillary-cellular distances, creating problems of poor diffusion and transport between the circulatory system and the functional cells (i.e. the cells within the organ). The wider the distances between the functional cells and the capillaries, the less oxygen and energy substrates are able to enter the cell and the less carbon dioxide and its acid by-products are able to leave. These events result in cellular anoxia, a cellular energy deficit, acidosis and possibly sequential organ failure.

In the past, others have approached the problem of albumin leakage and the concurrent creation of a third space through chemical or pharmacological means. The present invention approaches the problem as a biophysical phenomenon; the method employed to solve the problem involves using natural or synthetic macromolecules as sealants to inhibit the escape of albumin and other macromolecules. These macromolecules are effective because their configuration prohibits their escape through the enlarged capillary endothelial junctions.

SUMMARY OF THE INVENTION

The present invention provides a method of treating a human subject to prevent leakage of serum albumin and other macromolecules from capillary endothelial junctions during a period of increased capillary permeability. This method comprises administering to the human subject an effective capillary pore sealing amount of a macromolecule which is biodegradable, nontoxic, globular in shape, and has a molecular weight within the range from about 100,000 daltons to about 1,000,000 daltons, and a pharmaceutically acceptable carrier.

Also provided is a composition of matter useful for treating a human subject to prevent leakage of serum albumin from capillary endothelial junctions during a period of increased capillary permeability. This composition of matter comprises a fraction derived from hydroxyethyl starch.

DETAILED DESCRIPTION OF THE INVENTION

The present invention provides a method of treating a human subject to prevent leakage of serum albumin and other macromolecules from capillary endothelial junctions during a period of increased capillary permeability. This method comprises administering to the human subject an effective capillary sealing amount of a macromolecule which is biodegradable, non-toxic, globular in shape, with a molecular weight within the range from about 100,000 daltons to about 1,000,000 daltons, and a pharmaceutically acceptable carrier. Pharmaceutically acceptable carriers are known in the art to which the present invention pertains and include, but are not limited to, 0.01–0.1M, preferably 0.05M, phosphate buffer, Ringer's lactate, 5% dextrose, or normal saline.

In one embodiment of the invention, the macromolecule is a synthetic macromolecule. In another embodiment of the invention, the macromolecule is a naturally occurring macromolecule.

The method provided by the present invention may comprise administering to the human subject intravenously an effective capillary sealing amount of the macromolecule.

In one embodiment of the invention, the macromolecule comprises hydroxyethyl starch (HES). In another embodiment of the invention, the macromolecule is derived from HES. The macromolecule may comprise a fraction derived from HES having a molecular weight of less than about 50,000 daltons. Additionally, the macromolecule may comprise a fraction derived from HES having a molecular weight within the range from about 100,000 to about 300,000 daltons. Furthermore, the macromolecule may comprise a fraction derived from HES having a molecular weight greater than about 300,000. Moreover, the macromolecule may comprise a fraction derived from HES having a molecular weight within the range from about 300,000 to about 1,000,000 daltons.

In a further embodiment of the invention, the macromolecule comprises a dextran. In a preferred embodiment of the invention, the dextran has a molecular weight within the range from about 100,000 daltons to about 200,000 daltons. In a further preferred embodiment of the invention, the dextran has a molecular weight of about 500,000 daltons.

In yet another embodiment of the invention, the macromolecule comprises glycogen. In one embodiment, the glycogen has a molecular weight within the range from about 270,000 to about 350,000 daltons.

The present invention also provides a method of treating a human subject suffering from trauma, ischemia, vascular ischemia, burn-shock; undergoing treatment for organ preservation; or as part of a pre-surgical or post-surgical technique.

The present invention further provides a composition of matter useful for treating a human subject to prevent leakage of serum albumin and other macromolecules from capillary endothelial junctions during a period of increased capillary permeability which comprises a fraction derived from HES and a pharmaceutically acceptable carrier.

In one embodiment of the invention, the composition of matter comprises a fraction derived from HES and having a molecular weight less than of about 50,000 daltons. In another embodiment of the invention, the composition of matter comprises a fraction derived from HES and having a molecular weight within the range from about 100,000 daltons to about 300,000 daltons. In still a further embodiment of the invention, the composition of matter comprises a fraction derived from HES and having a molecular weight of greater than about 300,000 daltons. In yet another embodiment of a invention, the composition of matter comprises a fraction derived from HES having a molecular weight within the range from about 300,000 daltons to about 1,000,000 daltons.

Furthermore, the composition of matter provided by the present invention may comprise a fraction derived from HES which includes a biodegradable, macromolecular colloid, having a globular shape and a half-life of 17 days.

The methods of treating a human subject to inhibit the leakage of intracapillary serum albumin will be better understood by reference to the following examples, which are provided for purposes of illustration and are not to be construed as in any way limiting the scope of the invention, which is defined by the claims appended hereto.

EXAMPLE 1

Hespan® hydroxyethyl starch (American Critical Care Chicago, Ill.) which is described in U.S. Pat. No. 3,523,938 and which is about 0.7–0.8 degree hydroxyethlated, is a synthetic colloid. Hespan® was separated into three molecular weight fractions, i.e. $F_S$ (molecular weight of less than 50,000 daltons), $F_M$ molecular weight of about 100,000 daltons to about 300,000 daltons), and $F_L$ molecular weight of greater than 300,000 daltons). The fractionation of Hespan® was performed as follows:

Hespan® was filtered through a Diaflo Ultrafilter XM300>300,000 daltons (Amicon), for 4 hours. The filter chamber was placed on a magnetic stirrer under nitrogen gas pressure of 55 p.s.i. After 4 hours the unfiltered macromolecules were collected and labelled as the fraction $F_L$. The $F_L$ fraction consists of macromolecules of greater than 300,000 daltons. The filtrate (the material that passed through the filter) was made up of macromolecules of less than 300,000 daltons.

The filtrate from the Diaflo Ultrafilter XM300>300,000 daltons, was refiltered through a Diaflo Ultrafilter YM100>100,000 daltons (Amicon). The retained solution which did not pass through the filter consisted of macromolecules within the molecular weight range of about 100,000 daltons to about 300,000 daltons. This unfiltered solution was designated the FM fraction.

The filtrate that passed through the Diaflo Ultrafilter YM100>100,000 daltons, contained macromolecules of less than 100,000 daltons. This filtrate was refiltered through a Diaflo Ultrafilter XM50<50,000 daltons, and found to be almost totally filterable. The filtrate containing macromolecules of less than 50,000 daltons was designated FS.

Pentastarch® (American Critical Care) another hydroxyethyl starch which is about 0.4–0.5 degree hydroxyethylated, was separated and a fraction designated FLM (molecular weight of about 300,000 daltons to about 1,000,000 daltons) was obtained.

Pentastarch® was filtered through Diaflo Ultrafilter XM300>300,000 (Amicon), under the conditions described above. The retained solution was designated $F_{LM}$ and the filtrate was discarded. The $F_{LM}$ fraction contains macromolecules of about 300,000 daltons to about 1,000,000 daltons.

Applicants contemplate that the methods and compositions of matter provided by the present invention may also comprise the use of other commercially available hydroxyethyl starches.

EXAMPLE 2

Materials and Methods

Hespan® hydroxyethyl starch, a synthetic colloid, was separated into three molecular weight fractions $F_L$, molecular weight greater than 300,000 daltons; $F_M$, molecular weight of about 100,000 daltons to about 300,000 daltons; and $F_S$, molecular weight less than 50,000 daltons. The experiment involved 67 rats, unequally divided in 5 groups. Under anesthesia, the femoral veins of rats (240-260 grams) were catherized and a standard jejunal loop was placed in a petri dish over the abdomen. The five groups were injected with one of 5 solutions (with no duplications): 1) Ringer's lactate, (2) serum albumin 5%, (3) $F_L$ at 6% concentration, (4) $F_M$, at 6% concentration, (5) $F_S$ at 6% concentration. The injection volume was 2.5 ml. Then post injection blood samples and intestinal washings were taken. After the injections, the femoral veins of rats were scalded. Blood samples and intestinal washing were taken 15 minutes and 30 minutes post scald to determine the leakage volume of albumin and other macromolecules. Serum albumin ($C_P$) and albumin of the intestinal exudate ($C_L$) (the albumin content of the intestinal exudate is known to be very close to the lymph albumin concentration) were used to calculate the reflection coefficient, sigma (δ) for albumin, according to Patlak equation :

$$1 - \frac{C_L}{C_P}$$

Results

According to the values for each of the 5 groups, only the medium size macromolecules, i.e., macromolecules with a molecular weight of about 100,000 to about 300,000 daltons (corresponding to $F_M$), significantly decreased albumin leakage compared to Ringer's lactate, albumin, $F_L$, $F_S$, and other larger and smaller molecules.

| n = number of rats | Groups | Sigma Values prescald | Sigma Values 30 min. post-scald | Probability of error |
|---|---|---|---|---|
| 10 | Ringer's | 0.93 ± .03 | 0.39 ± .11 | |
| 15 | Albumin | 0.94 + .02 | 0.58 + .05 | <0.05 |
| 13 | HES $F_L$ | 0.95 + .02 | 0.51 + .12 | <0.05 |
| 16 | HES FM | 0.95 + .04 | 0.82 + .05 | <0.05 |
| 13 | HES $F_S$ | 0.96 + .03 | 0.61 + .08 | <0.05 |

EXAMPLE 3

The animal models used in this experiment were 81 female Sherman rats weighing between 180-200 grams. The rats were unequally divided into 7 groups. The animals were anesthetized with ether followed by chloral hydrate to maintain appropriate anesthesia. All rats underwent femoral vein cannulation.

Group I consisted of 16 rats, all scalded (60% of its body surface area) on a Walker Wooden Template at 95° C. for 20 seconds. This group served as the control group suffering 100% mortality within 24 hours.

Group II consisted to 15 rats each receiving an intravenous injection of HES (2.5% of its body weight) and then scalded over 60% of its body surface area on a Walker Wooden Template for 20 seconds at 95° C.

Group III consisted of 10 rats. Each rat received an intravenous solution of serum albumin 5% and then scalded (60% of its body surface area) on a Walker Wooden Template for 20 seconds a 95° C.

Group IV consisted of 10 rats. Each rat received Ring's lactate intravenously and then scalded (60% of its body surface area) on a Walker Wooden Template for 20 seconds at 95° C.

Results

Group I: The control group suffered a 100% mortality rate 24 hours after the burn.

Group II: Six of the fifteen rats died 24 hours after the burn, despite the pre-burn intravenous solution of 6% HES. The mortality rate for Group II is 40%, the survival rate is 60%.

Group III: Eight of the ten rats died 24 hours after the burn, despite the pre-burn intravenous solution of serum albumin 5%. The mortality rate is 80%; the survival rate is 20%.

Group IV: Eight of the ten rats died 24 hours after the burn despite the pre-burn intravenous solution of Ringer's lactate. The mortality rate is 80%; the survival rate is 20%.

TABLE 1

|  | Control Group I | Group II | Pre-Burn Group III | Group IV |
| --- | --- | --- | --- | --- |
| n | 16 | 15 | 10 | 10 |
| Deaths | 16 | 6 | 8 | 8 |
| Mortality | 100% | 40% | 80% | 80% |
| Survival | 0% | 60% | 20% | 20% |

EXAMPLE 4

180 adult male Sprague-Dawby rats weighing between 240–260 grams were divided into 9 groups, 20 rats per group. Anesthesia was induced by Metofan inhalation supplemented by an intraperitoneal injection of chloral hydrate 4% (0.3 mg/kg). The left hind leg was shaved up to the groin and the limb was rendered ischemic by the application of an elastic rubber band (standard #12 pure crepe 9/86), looped three times, just above the knee joint. The rats were re-anesthetized, 2 hours after the first application of anesthesia, by using a #25G ⅜ inch butterfly needle via the dorsal vein of the penis.

Each group received one of nine solutions, with no duplications. The nine solutions are: (1) 5% albumin, (2) Ringer's Lactate, (3) HES $F_S$, (4) HES $F_M$, (5) HES $F_L$, (6) HES $F_{LM}$, (7) glycogen (less than 300,000 daltons), (8) glycogen (greater than 300,000 daltons), and (9) dextran (150,000 daltons).

The injection volume of each solution was 2.5 cc (representing 10% of a rat's body weight). (An equivalent amount of 6% HES for a human would be measured by administering a volume equal to 10% of the human subject's body weight.) Five minutes after the injection, the rubber tourniquet was released. After the lapse of another five minutes, the rats were intravenously injected with 1cc of Evan's Blue Dye, 0.5%. There was a 24 hour observation period followed by euthanasia. Euthanasia was induced by the intraperitoneal injection of a solution of T-61.

The gastronemius muscle was isolated and dissected bilaterally. One part of the bilateral dissection was weighed and then placed in an oven (for dry weighing) at 250° C. for 48 hours. It was then transferred to a test tube containing 3 milliliters 0.75N nitric acid, left overnight, and then thoroughly crushed with a glass stirrer to leach out the potassium. This action produced a solution which was measured on a Beckman Astra Machine to determine the potassium content. The second part of the muscle was sent for histopathological examination in Bouine's solution.

In this example the extremity without a tourniquet served for comparison and the following muscle characteristics were studied on both legs with a tourniquet and those without: (1) whole muscle weight; (2) moisture content: (3) total potassium content and (4) histopathological characteristics.

Results

A small number of animals were excluded from the study due to technical problems.

No mortalities directly attributable to the injection of macromolecules were observed. However, some animals randomly developed paresis of the ischemic leg. Any degree of significant distress was alleviated by periodic intraperitoneal injections of chloral hydrate.

The muscles of the leg with the tourniquet were stained blue due to the dye injection. The groups injected with HES $F_{LM}$ and $F_M$ showed a degree of staining that was less intense than those injected with the 7 remaining solutions. The le9 without a tourniquet(i.e. did not suffer from ischemia) did not stain blue despite the injection of dye.

In Table 1, note that rats who received HES $F_{LM}$ ($p<0.005$) had a significantly lower muscle weight than rats who received the albumin or Ringer's Lactate solution). These values indicate that rats injected with $F_{LM}$ did not experience the weight gain that is associated with leakage of fluids from the capillaries into the interstitium.

TABLE 1

| | TOTAL MUSCLE WEIGHT | | |
| --- | --- | --- | --- |
| Groups (n = 16–20 rats) | Mean and Standard Deviation (in grams) | p Value = probability of error | |
| | | 5% Albumin | Ringer's Lactate |
| 5% Albumin | 2.62 + 0.27 | — | — |
| Ringers's Lactate | 2.50 ± 0.22 | — | — |
| HES FLM | 2.34 ± 0.23 | <0.005 | <0.005 |
| HES $F_M$ | 2.42 ± 0.31 | <0.05 | <0.05 |
| HES FL | 2.49 ± 0.21 | n.s. | n.s. |
| HES $_{FS}$ | 2.61 ± 0.19 | n.s. | n.s. |
| Glycogen 100,000–300,000 daltons | 2.60 ± 0.24 | n.s. | n.s. |
| Glycogen greater than 300,000 | 2.58 ± 0.35 | n.s. | n.s. |
| Dextran about 150,000 daltons | 2.55 ± 0.28 | n.s. | n.s. | n.s.: Not Significant

In Table 2, the moisture content was comparable for all the groups except $F_{LM}$ and $F_M$. Less moisture content means less leakage of fluids from the capillaries into the interstitium.

TABLE II

MOISTURE CONTENT

| Groups | Mean and Standard Deviation (in %) | p Value = probability of error | |
|---|---|---|---|
| | | 5% Albumin | Ringer's Lactate |
| 5% Albumin | 84.16 + 2.30 | — | — |
| Ringers's Lactate | 84.69 ± 1.35 | — | — |
| HES FLM | 80.75 ± 4.30 | <0.005 | <0.005 |
| HES $F_M$ | 82.79 ± 2.56 | <0.05 | <0.05 |
| HES FL | 83.59 ± 2.05 | n.s. | n.s. |
| HES $_{FS}$ | 84.94 ± 1.79 | n.s. | n.s. |
| Glycogen 100,000-300,000 daltons | 83.22 ± 2.89 | n.s. | n.s. |
| Glycogen greater than 300,000 daltons | 84.88 ± 2.04 | n.s. | n.s. |
| Dextran about 150,000 daltons | 84.12 ± 1.69 | n.s. | n.s. | n.s.: Not Significant

The differences in potassium content between muscles with and without a tourniquet in Table 3 corroborated the findings in Tables 1 and 2 that rats injected with HES $F_{LM}$ and $F_M$ demonstrated less leakage of intercapillary fluids and better preservation of cellular integrity of the muscle. In Table III, the smaller the potassium difference, between muscles with the tourniquet and those muscles without the tourniquet, the less the intracapillary fluid loss. Less intracapillary fluid loss means less problems with close compartment syndrome; a syndrome which leads to muscle necrosis and therefore, loss of potassium.

TABLE III

Differences In Potassium Content Between Tourniquet and Non-Torniquet Muscles

| Groups | Mean and Standard Deviation (in milli equivalents per deciliter) | p Value = probability of error | |
|---|---|---|---|
| | | 5% Albumin | Ringer's lactate |
| 5% Albumin | 31.99 + 6.6 | — | — |
| Ringer's Lactate | 39.26 ± 6.85 | — | — |
| HES FLM | 18.54 ± 9.27 | <0.005 | <0.005 |
| HES $F_M$ | 17.3 ± 10.7 | <0.05 | <0.05 |
| HES FL | 34.78 ± 11.27 | n.s. | n.s |
| HES $_{FS}$ | 38.78 ± 7.6 | n.s. | n.s. |
| Glycogen 100,000-300,000 daltons | 33.96 ± 8.44 | n.s. | n.s. |
| Glycogen greater than 300,000 daltons | 33.96 ± 8.44 | n.s. | n.s. |
| Dextran about 150,000 daltons | 32.52 ± 7.42 | n.s. | n.s. | n.s.: Not Significant

Microscopic studies showed discernible differences between the rats injected with HES $F_{LM}$ and $F_M$ compared to the rats injected with the other seven solutions. Edema and necrosis was only mild to moderate in the rats injected with HES $F_{LM}$ or $F_M$ whereas the remaining rats showed moderate to severe edema and necrosis of the gastronemius muscle.

EXAMPLE 5

Twenty-five female Sherman rats were unequally divided into two groups. Group 1 contained 11 rats, Group 2 contained 14. The rats were placed under anesthesia and the femoral veins were catherized after which a standard jejunal loop was placed in a petri dish over the abdomen. Then group 1 rats were injected with dextran (100,000-200,000 daltons) and group 2 rats were injected with dextran (500,000 daltons). Postinjection blood samples and intestinal washings were taken and 30 minutes after the washings the femoral veins were scalded. After another 30 minutes a second round of blood samples and intestinal washings were obtained

Results

The reflection coefficient (sigma value) 30 minutes prior to the scald-burn was measured at 0.94±0.03 in Group 1 rats and 0.95±0.05 in Group 2 rats. Thirty minutes after the scald-burn the sigma value for Group 1 rats equaled 0.74±0.02 and for Group 2 rats equaled 0.85±0.6 The probability of error in the 30 minutes post-burn measurements is 0.05 or 5%.

By using the Patlak equation for solute reflux across a microvascular membrane the reflection coefficient for total plasma of the rats was measured. The reflection coefficient (sigma value) is the measure of a membrane's ability to restrict the passage of protein molecules. If the protein molecules are totally reflected compared to water, the value is one. If all the protein molecules pass through the membrane the sigma value is zero. Therefore, the reflection coefficient for plasma is:

$$= 1 - \frac{C_L}{C_p}$$

Comparing sigma values for both groups 30 minutes post burn note that rats injected with Dextran (500,000 daltons) had a higher sigma value therefore less protein molecules passed through the membrane. The data indicates that Dextran (500,000 daltons) is a more effective sealant of capillary endothelial junctions than Dextan (100,000-200,000 daltons).

| Clapillary Oncotic Pressure versus macromolecular size | | | | |
|---|---|---|---|---|
| N = # of rats | Macromolecule | Value Reflection Coefficients | Value 30' | P = Proability of error |
| 11 | Dextran 100,000 to 200,000 daltons | 0.94 ± 0.03 | 0.74 ± 0.02 | 0.05 |
| 14 | Dextran 500,000 daltons | 0.94 ± 0.05 | 0.85 ± 0.06 | |

DISCUSSION

This method of using macromolecules to reduce the normal effect of increased capillary permeability has wide applications in the biological sciences. A small, concentrated volume of useful but harmless macromolecules will make a major medical impact when applied immediately after traumas such as in early shock, in burns, in organ preservation and before major surgery. The significant results are: reduction of edema and myonecrosis; which reduces the pain and discomfort in surgical patients and produces rapid recovery and early discharge from the hospital.

Scientific studies have shown that traumas such as burns and anoxia cause the enlargement of capillary endothelial junctions which leads to leakage of circulatory fluids and albumin into a nonfunctional "third space". This phenomenon occurs as part of a biochemical chain of events initiated by inflammatory mediators such as histamines, kinins, kalekreins, bradykinins, proteolytic enzymes, prostaglandins, etc.

Examples 1-4 illustrate the mechanism of preventing albumin leakage is through occlusion of the capillary endothelial junctions by these macromolecules and not through maintenance of a particular capillary oncotic pressure within the vessel. If it is capillary oncotic pressure which prevents the leakage of albumin and fluids then the smaller macromolecules should do a better job of inhibiting intracapillary leakage than the larger macromolecules since oncotic pressure is determined by the number of molecules and their electric charges. The smaller the molecules the greater the number per given volume and the greater the oncotic pressure. Example I shows that with various size fractions of hydroxyethyl starch the smaller molecular weight fractions and the very large molecular weight fractions do not form as good a seal as the medium ranged molecules.

In Example 2, the jejunal loop study, it appears that the very large molecules (over 500,000-600,000 daltons) and the very small molecules (less than 150,000 daltons) do not effectively serve the sealing process.

Example 3 illustrates that macromolecules between the range of 300,000 daltons to 1,000,000 daltons are more effective than the small molecules (less than 300,000 daltons) to act as capillary seals. Moreover, Example 3 illustrates an effective method of treating a human subject suffering from states of severe ischemia like myocardial or cerebrovascular ischemia; burnshock; or as a treatment for organ preservation or transplantation; or as part of a pre-surgical and postsurgical technique.

Example 4 shows that changes in the reflection coefficient is not determined by capillary oncotic pressure. Rats injected with dextran (100,000-200,000 daltons) received more than twice the number of molecules than the group injected with dextran (500,000 daltons) since both dextran solutions were prepared as 6% solutions in normal saline and both rat groups received an identical volume. The number of molecules is the primary determinant of capillary oncotic pressure therefore, rats injected with dextran (100,000-200,000 daltons) should have less leakage of albumin and a larger sigma value. However, the opposite is the case. It appears that the larger, less branched, globular, dextran (500,000 daltons) molecules are better sealants against the escape of intracapillary albumin and other macromolecules than dextran (100,000-200,000 daltons).

Vascular ischemia, like other types of inflammation, results in capillary endothelial damage followed by vascular leakage of albumin and fluids into the interstitium. The greater the volume of albumin and fluids into the interstitium the greater the "third space" and its concurrent problems of poor diffusion of oxygen and energy substrates into the cells and the carbon dioxide and metabolic acids out of the cells. The process of vascular leakage has been widely studied and shown to be due to endothelial cell contraction, leading to separations of intercellular junctions and formation of pores. This has been established to occur almost exclusively in the post capillary (pericytic) venules with a diameter within the 10-50 micron range (1-6).

HES is an artificial colloid with an average molecular weight of 450,000 daltons. The molecular range varies from 10,000 daltons to 3,500,000 daltons. It is derived from a waxy starch composed entirely of amylopectin. The colloidal properties of 6% hetastarch approximate those of human albumin which accounts for 80% of the colloidal osmotic pressure of plasma under normal circumstances (7). Although variable, greater than 90% of HES is eliminated with a half life of 17 days (7). Some adverse reaction to hetastarch have been observed in regards to allergy and coagulopathy but was not of any significance (8-10). As to severe anaphylactoid reactions the incidence was 0.006% compared to albumin's 0.003% and dextran's 0.008% (13).

Despite its extensive clinical use, HES has not been observed to be more than merely exerting a colloidal oncotic pressure when compared to albumin (8-12). This may be in part due to the sealing process in separated endothelial junctions which requires a range of macromolecules with a specific size and shape. Since the molecular distribution of Hespan ® constitutes a mixed bag of varying size molecules and since it has a moderate number of small sized molecules greater than 300,000 daltons, it may have benefits over the use of many other colloids.

Experiments with macromolecules other than HES have produced promising substances, as illustrated by their high sigma values. These macromolecules are dextran, certain globulins and most significantly glycogen. The data found in examples 1, 2, 3 and 4 indicates that HES $F_S$, $F_M$, $F_L$ and $F_{LM}$, dextran about (500,000 daltons) and glycogen (>300,000 daltons) significantly reduce the leakage of serum albumin from burn injury of jejunum and ischemic injury of skeletal muscles of rat hind legs.

It must be pointed out that different organs have varying endothelial junction tightness (or looseness). For example, the brain has the tightest endothelial junctions while the liver has the most loose. The degree of injury or effect of inflammary mediators may produce separation of capillary endothelial cell junctions in varying sizes that may require a variable range of molecular sealants to achieve an effective seal.

REFERENCES

1. Joris, I., Majno, G., Ryan, G. B.: Endothelial contraction in vivo: A study of the rat mesentery. Virchows Arch (Cell Pathol.) 1972, 12:73-83.
2. Horan, K. L., Adamski, S. W., et al., Evidence that prolonged histamine suffusions produce transient increases in vascular permeability subsequent to the formation of venular macromolecular leakage sites. Proof of the Majno-palade hypothesis. American Journal of Pathology 1986, 124:570-576.
3. Majno, G., Palade, G. E.: Studies on inflammation: 1. The effect of histamine and serotonin on vascular permeability: an electron microscopic study. J. Biophys. Biochem. Cytol 1961, 11:571-605.
4. Lelcuk, S., et al.: Thromboxane A2 moderates permeability after limb ischemia. Ann Surg 1985, Nov.; 202(5):642-646.
5. Joris, I., et al.: The mechanism of vascular leakage induced by leukotriene E4 Endothelial contraction. Am. J. of Pathology 1987, 126(1): 19-24.
6. Grega, G. J.: Role of the endothelial cell in regulation of microvascular permeability to molecules. Introductory remarks. Fed. Proc. 1986 Feb. 45(2):75-76.
7. Maier R. V., Carrico, C. J.: "Artifical plasma expanders: Hetastarch and Dextran" in Developments in Resuscitation Advances in Surgery 1986, 19:290-296.

8. Moggio, R. A., et al.: Hemodynamic comparison of albumin and hydroxyethyl starch in postoperative cardiac surgery patients. Crit. Care Med. 11:943, 1983.

9. Kirklin, J. K., Lell, W. A., Kouchoukos, N. T.: Hydroxyethyl starch versus albumin for colloid infusion following cardiopulmonary bypass in patients undergoing myocardial revascularization. Ann Thorac. Surg. 1984, 37:40.

10. Diehl, J. T., Lester, J. L. III, Cosgrove, D. M.: Clinical Comparison of hetastarch and albumin in postoperative cardiac patients. Ann. Thorac. Surg., 1982, 34:674.

11. Rackow, E. C., Falk, J. L., Fein, A., et al.: Fluid resuscitation in circulatory shock: A comparison of the cardiorespiratory effects of albumin, hetastarch, and saline solutions in patients with hypovolemic and septic shock. Crit. Care Med. 983. 11:839.

12. Puri, V. K., Howard, M , Paidipaty, B., et al.: Comparative studies of hydroxyethyl starch and albumin in hypovolemia Crit. Care Med. 1982, 0:230.

13. Ring J., Messmer K.: Incidence and severity of anaphylactoid reactions to colloid volume substitutes. Lancet 1977, 1:466.

What is claimed is:

1. A method of treating a human subject suffering from trauma to prevent leakage of serum albumin from capillary endothelial junctions during a period of increased capillary permeability which comprises administering to the human subject an effective capillary sealing amount of a macromolecule which is biodegradable, non-toxic, globular in shape, and has a molecular weight within the range above 100,000 daltons to about 1,000,000 daltons in a pharmaceutically acceptable carrier.

2. A method of claim 1, wherein the human subject is suffering from trauma associated with a burn, shock, ischemia, organ transplantation, or a pre- or postsurgical technique.

3. A method of claim 1, wherein the macromolecule is administered intravenously.

4. A method of claim 1, wherein the macromolecule is derived from hydroxyethyl starch.

5. A method of claim 4, wherein the macromolecule comprises a fraction derived from hydroxyethyl starch and has a molecular weight within the range from about 100,000 to about 300,000 daltons.

6. A method of claim 4, wherein the macromolecule comprises a fraction derived from hydroxyethyl starch and has a molecular weight within the range from about 300,000 to about 1,000,000 daltons.

7. A method of claim 1, wherein the macromolecule comprises a dextran.

8. A method of claim 7, wherein the dextran has a molecular weight within the range from about 100,000 daltons to about 200,000 daltons.

9. A method of claim 7, wherein the dextran has a molecular weight of about 200,000 to about 400,000 daltons.

10. A method of claim 7, wherein the dextran has a molecular weight of about 500,000 daltons.

11. A method of claim 1, wherein the macromolecule comprises glycogen.

12. A method of claim 11, wherein the glycogen has a molecular weight within the range from about 270,000 to about 350,000 daltons.

* * * * *